US009820723B2

United States Patent
Lee

(10) Patent No.: US 9,820,723 B2
(45) Date of Patent: *Nov. 21, 2017

(54) POSITIONING GUIDE APPARATUS WITH FRICTION LOCK

(71) Applicant: Choon Kee Lee, Denver, CO (US)

(72) Inventor: Choon Kee Lee, Denver, CO (US)

(*) Notice: Subject to any disclaimer, the term of this patent is extended or adjusted under 35 U.S.C. 154(b) by 937 days.

This patent is subject to a terminal disclaimer.

(21) Appl. No.: 14/097,228

(22) Filed: Dec. 4, 2013

(65) Prior Publication Data

US 2015/0150631 A1 Jun. 4, 2015

(51) Int. Cl.
| | | |
|---|---|---|
| A61B 8/00 | (2006.01) |
| A61B 10/04 | (2006.01) |
| A61B 8/08 | (2006.01) |
| A61B 17/34 | (2006.01) |
| A61B 17/00 | (2006.01) |
| A61B 90/00 | (2016.01) |

(52) U.S. Cl.
CPC ............ *A61B 10/04* (2013.01); *A61B 8/0841* (2013.01); *A61B 17/3403* (2013.01); *A61B 8/4209* (2013.01); *A61B 8/4236* (2013.01); *A61B 2010/045* (2013.01); *A61B 2017/00199* (2013.01); *A61B 2017/3413* (2013.01); *A61B 2090/067* (2016.02)

(58) Field of Classification Search
CPC .... A61B 2017/3409; A61B 2017/3413; A61B 90/11
See application file for complete search history.

(56) References Cited

U.S. PATENT DOCUMENTS

| | | | | |
|---|---|---|---|---|
| 4,058,114 A | * | 11/1977 | Soldner | A61B 8/0833 600/461 |
| 5,100,387 A | * | 3/1992 | Ng | A61B 10/0283 600/578 |
| 5,623,931 A | | 4/1997 | Wung | |
| 5,941,889 A | | 8/1999 | Cermak | |
| 6,203,499 B1 | | 3/2001 | Imling | |
| 6,475,152 B1 | | 11/2002 | Kelly, Jr. | |
| 6,485,426 B2 | * | 11/2002 | Sandhu | A61B 8/0833 600/461 |
| 7,691,066 B2 | | 4/2010 | Kosaku | |
| 7,846,103 B2 | | 12/2010 | Cannon, Jr. | |
| 7,976,469 B2 | | 7/2011 | Bonde | |
| 8,057,487 B2 | | 11/2011 | Chu | |
| 8,073,592 B2 | | 12/2011 | Cermak | |
| 8,118,743 B2 | | 2/2012 | Park | |

(Continued)

FOREIGN PATENT DOCUMENTS

| | | |
|---|---|---|
| CN | 201968836 U | 9/2011 |
| DE | 19808220 A1 | 9/1999 |
| DE | 10015510 A1 | 4/2001 |

*Primary Examiner* — Rajeev Siripurapu

(57) ABSTRACT

The present invention presents an apparatus and methods to guide insertion of invasive devices to a tissue target of a living body. The apparatus comprises a positioning guide control assembly and a positioning guide assembly that is operably detachable from the control assembly, and rotationally adjustable and lockable. The positioning guide control assembly releasably houses a ultrasound transducer head and measures an insertion length and an insertion angle of an invasive device placed in the positioning guide assembly to reach the tissue target.

4 Claims, 11 Drawing Sheets

(56) References Cited

U.S. PATENT DOCUMENTS

| | | |
|---|---|---|
| 8,216,149 B2 | 7/2012 | Oonuki |
| 8,241,301 B2 | 8/2012 | Zhang |
| 8,257,264 B2 | 9/2012 | Park |
| 8,496,593 B2 | 7/2013 | Park |
| 8,574,160 B2 | 11/2013 | Gorzitze |
| 2002/0058872 A1 | 5/2002 | Steininger |
| 2007/0073155 A1 | 3/2007 | Park |
| 2011/0313293 A1 | 12/2011 | Lindekugel |
| 2012/0059260 A1 | 3/2012 | Robinson |
| 2013/0066192 A1 | 3/2013 | Sarvestani |
| 2013/0066232 A1* | 3/2013 | Schoepp ............ A61B 17/3403 600/567 |
| 2013/0197355 A1 | 8/2013 | Lee |
| 2013/0225984 A1 | 8/2013 | Cheng |

* cited by examiner

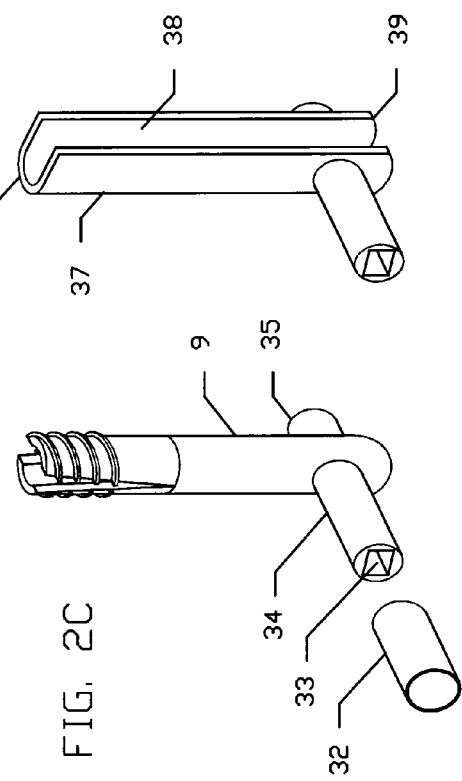
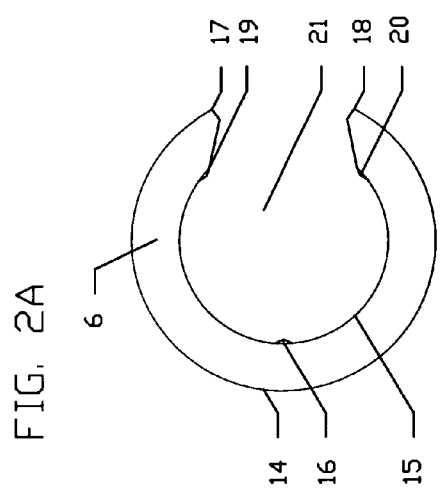
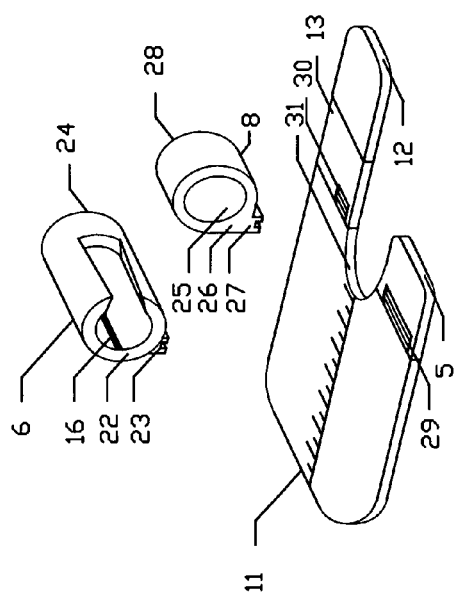

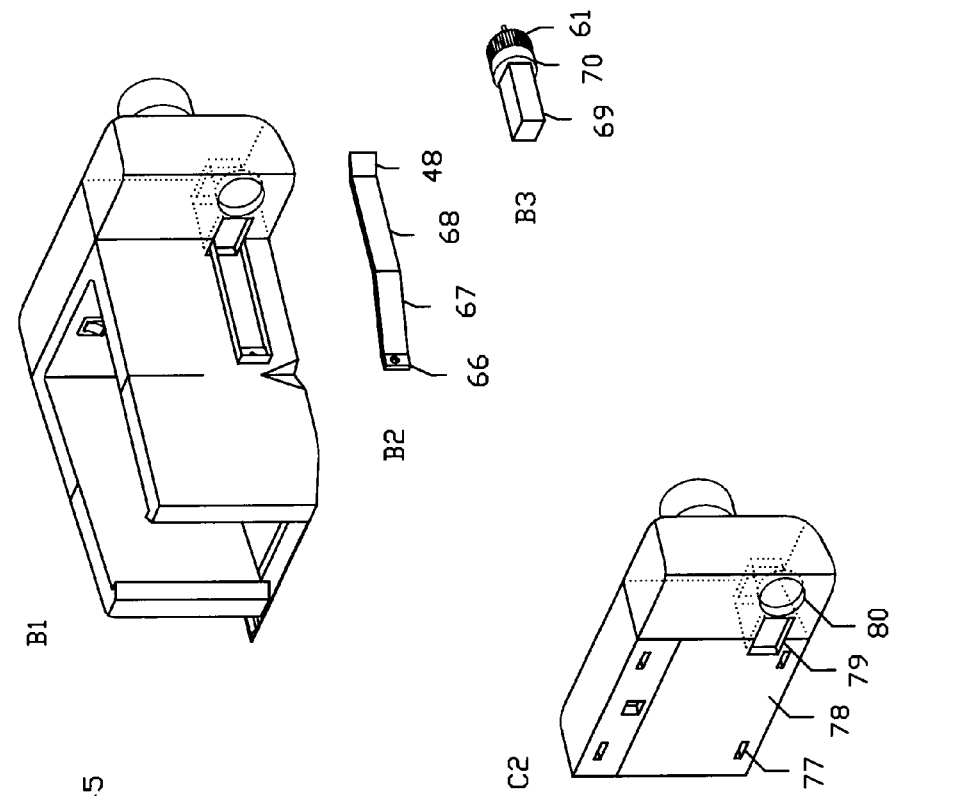
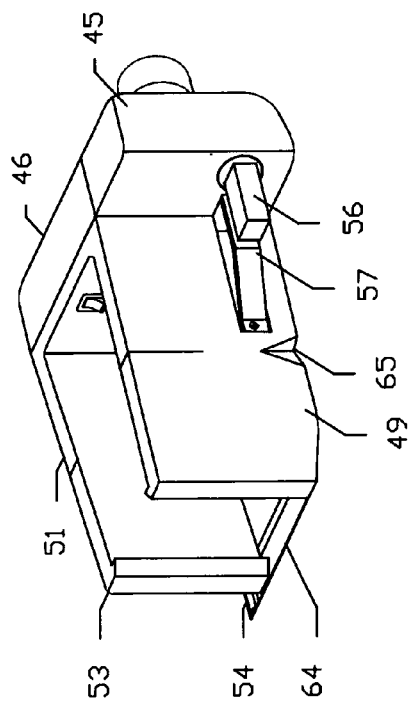
FIG. 5A  FIG. 5B  FIG. 5C

B-1    B-2

A

POSITIONING GUIDE APPARATUS WITH FRICTION LOCK

TECHNICAL FIELD

The present invention relates generally to the field of positioning guidance of insertion of invasive devices in a living body for medical purpose. More specifically, the present invention provides an apparatus and methods to assist introduction of tubular devices into a tissue using ultrasound.

BACKGROUND OF THE INVENTION

Procurement of a tissue sample from a living body is one most important step toward diagnosis of and management plans for a disease in a range of medical fields. Traditionally, both open surgical biopsy and core needle biopsy techniques have been available for tissue biopsy. Open surgical biopsy, however, requires anesthesia and a relatively large incision on skin yet discovers a benign lesion in many patients who end up with surgical scars. Compared to open surgical biopsy, core needle biopsy has been shown to minimize complication rates while achieving high rates of sensitivity and specificity of correct tissue diagnosis equivalent to those following the open surgical biopsy. Regarding techniques for core needle biopsy, image-guided needle biopsy techniques have been shown to be superior to freehand, unguided biopsy techniques in terms of diagnostic sensitivity.

Visual guidance using ultrasound images has been successfully used for inserting core biopsy needle into tissue, resulting in high rates of sensitivity of tissue diagnosis. For an example, sensitivity of a ultrasound guided core needle biopsy for women with a suspicious lesion in breast has been above 97%, compared favorably to 86% of a freehand biopsy technique. The majority of ultrasound guidance devices use a separate needle guidance device reversibly attachable to an ultrasound transducer head. An operator takes a look at ultrasound images of a target on a monitor of an ultrasonographic apparatus, and visually estimates an approximate angle that a core biopsy needle needs to be at in relation to the target. While holding the ultrasound transducer by one hand and monitoring ultrasound images, the operator then pushes in the core biopsy needle using the other hand.

One drawback of the visual guidance for needle insertion is that since it depends on an operator's subjective visual estimation of an angle and length of a biopsy needle, there is a steep learning curve to achieve enough dexterity and coordination of both hands for correct introduction of the biopsy needle. Not infrequently, several insertion attempts are made before finding a suitable path of the needle toward the target, which increases chances of shearing off important tissue structure such as lymphatics and blood vessels. Sometimes an assistant would be necessary, who would continuously scan a target area while an operator tries to introduce a needle to the target. The other difficulty of the visual ultrasound guidance comes from a need of hand-held positioning of a ultrasound transducer on a skin overlying the target, which requires a good hand-eye coordination and a well-trained hand holding steady the transducer throughout the procedure regardless of patient's movements like breathing. These technical difficulties could increase chances of bleeding and infection at a biopsy site, and increase chances of spillage of malignant cells or of infectious germs from the target to adjacent areas that are not involved by a cancer or an infection, respectively.

Increase in size and number of a core needle biopsy sample has been associated with increase in both the diagnostic sensitivity and specificity. Yet in practice, it has been limited by increase in rates of complications such as bleeding, internal tissue injury and infection. Unless a single introduction of a core needle procures multiple samples of a sufficient size, repetitive manual insertions of the needle under a visual guidance using ultrasonogram would increase chances of these complications. Vacuum assisted biopsy has been developed to procure multiple samples, yet it may not be applicable for internal organs such as lungs due to a concern of significant pneumothorax and bleeding. Organs having a high density of blood vessels in tissue such as liver or kidneys may not be suitable for vacuum assisted biopsy since there would be serious bleeding consequences from damaged blood vessels following the procedure.

These technical challenges may be overcome if visual ultrasound guidance provides an operator with objective numerical positioning data such as a length of a needle to reach a target from a skin and a trigonometric angle between a longitudinal axis of the needle and a horizontal axis of an ultrasound transducer visualizing the target. In addition to a visual information seen on a monitor, the data should increase chances of the needle reaching the target with less frequent attempts. Complications may also be reduced if the biopsy needle is guided in a positioning guidance device that is temporarily and firmly fixed to the skin overlying the target, which maintains position of the needle steady during the biopsy procedure.

Modern applications of visual positioning guidance for invasive procedures have evolved to combine ultrasound guidance with either CT (Computer-Tomogram)—or MRI (Magnetic Resonance Imaging) visualization, to increase sensitivity of the procedures. Yet concurrent visualization by both ultrasonogram and CT or MRI, which is regarded as most ideal for visualization, is hampered by a need to combine two imaging data in one display. Furthermore, MRI precludes concurrent use of metallic devices for ultrasonogram as the metallic components of ultrasonogram devices interfere with electromagnetic fields of the MRI.

SUMMARY OF THE INVENTION

The present invention provides an apparatus that generates a set of numerical data of a length of a biopsy needle to be inserted in a patient's tissue and a trigonometric angle between a longitudinal axis of the needle and a horizontal axis of an ultrasound transducer visualizing a target. The invention provides a means to steady the biopsy needle at a site of needle entry to the tissue, without a need to rely on an operator's hand. The invention also allows ultrasound positioning to be objectively verified by either CT or MRI visualization. The apparatus comprises a positioning guide control assembly and a positioning guide assembly that is releasably detachable from the positioning guide control assembly and operable. The positioning guide control assembly releasably houses a ultrasound transducer head and controllably rotates a part of the positioning guide assembly. The positioning guide assembly is reversibly anchorable to a skin overlying the target.

In one embodiment, the positioning guide control assembly is provided in one or a plurality of configurations including a three-compartment configuration which comprises a transducer housing enclosure, a power and electronic control assembly and a positioning controller assembly. The transducer housing enclosure is provided in an open box configuration with its top and bottom portions open to allow a proximal portion of the transducer to slip in and out of said enclosure through the top portion and to allow a face portion of the transducer to contact a skin through the bottom portion that releasably holds a solid gel panel in between of the face portion and the skin. The transducer housing enclosure is configured to hold fast the proximal portion of the transducer in a manner to align longitudinal and horizontal axes of the transducer in parallel with longitudinal and horizontal axes of said transducer housing enclosure, respectively. A medial wall of the transducer housing enclosure adjoins a vertical sidewall of the power and electronic control assembly.

In one embodiment, the power and electronic control assembly is provided in one or a plurality of configurations including a rectangular box configuration which has a segment digital display on a top portion. An integrated circuit board is located under and electronically connected to the segment digital display. A compartment for replaceable batteries is located below the integrated circuit board and connects batteries electrically with both the integrated circuit board and segment digital display. An anterior sidewall of the power and electronic control assembly adjoins a posterior sidewall of the positioning controller assembly.

In one embodiment, the positioning controller assembly is provided in one or a plurality of configurations including a rectangular box configuration which encloses a gearbox with its rotation center aligned horizontally and which has a pass-through horizontal conduit for a lock and release lever for the positioning guide assembly. The gearbox comprises a main driving gear connected through an input shaft to a rotatable knob located outside a lateral sidewall of the rectangular box, a parallel driven gear with its output shaft protruding through a medial vertical sidewall of said rectangular box and a pinion located in between of the driving and driven gears. The lock and release lever is irreversibly and insertably attached to a horizontal slot located on an outer surface of an anterior sidewall of the transducer housing enclosure and passes in part from an aperture located in a portion of a medial sidewall of said positioning controller assembly through the horizontal conduit to an aperture in an outer surface of a lateral sidewall of said positioning controller assembly.

In one embodiment, the output shaft of the driven gear is provided in one or a plurality of configurations including a longitudinal bar having more than two internal angles on cross-section of said bar. The output shaft releasably is inserted in a horizontal slot of a rotation cylinder of the positioning guide assembly. The rotation cylinder irreversibly is connected at a right angle to a lower outer wall of a tubular positioning guide of said positioning guide assembly. The rotation cylinder is rotated along the longitudinal axis of the output shaft by rotation of the rotatable knob that transmits rotation to the driven gear via the pinion. In one embodiment, the rotatable knob is configured to be calibrated for rotation by one or a plurality of methods, including a manual measurement using a dial marked in circle surrounding said knob on the lateral sidewall of said positioning controller assembly and an electronic measurement by an angle encoder axially connected to said knob via the input shaft and located inside said positioning controller assembly. The angle encoder is electronically connected to the power and electronic control assembly that displays numerical information about angular displacement of the rotation cylinder and distance from a rotation center of the rotation cylinder to a target. In another embodiment, a horizontal axis of the transducer is used as a reference axis for the rotatable knob to calibrate angular displacement of the tubular positioning guide and a longitudinal axis of the transducer is used for a reference axis for the rotation cylinder to align a longitudinal axis of the tubular positioning guide with said longitudinal axis of the transducer.

In one embodiment, the positioning guide assembly is provided in one or a plurality of configurations, including a cross configuration which comprises an upright tubular positioning guide and a pair of transverse cylinders irreversibly attached at a right angle to each opposite side of a lower portion of the outer wall of the tubular positioning guide, respectively. One transverse cylinder serves for rotation of the tubular positioning guide and the other transverse cylinder provides the tubular positioning guide with stability. Each transverse cylinder is slidably and rotatably housed in a horizontally tubular cylinder holder that is fixedly attached to a base panel located vertically below said transverse cylinder. A rotation cylinder holder has a horizontal slot for a length to accommodate a part of the lock and release lever, which faces the outer wall of the anterior sidewall of the transducer housing enclosure. An inner wall of the rotation cylinder holder has a plurality of substantially linear threads. In between of an outer circumferential wall of the rotation cylinder and the inner wall of the rotation cylinder holder, a thin nonslip tubular elastomer is provided, encasing the outer wall of said rotation cylinder. The horizontal slot of the rotation cylinder holder is reversibly and circumferentially expandable to a degree upon engagement with the lock and release lever, which widens an inner tubular space of said rotation cylinder holder. Widening of the inner tubular space allows friction-less rotation of both the elastomer and rotation cylinder inside said rotation cylinder holder. Disengagement of the lock and release lever shrinks the circumference of said tubular space, which then holds fast both the tubular elastomer and rotation cylinder together. The rotation cylinder is fastened by friction generated by the circumferentially squeezed tubular elastomer encasing said rotation cylinder. A transverse stabilizer cylinder slides in a tubular space of a stabilizer cylinder holder and stabilizes the tubular positioning guide on rotation. A mid portion of the base panel is configured to provide an open space through which a needle passes from the tubular positioning guide to a target. An opposite side of the base panel to the cylinder attachment side is configured to provide reversible adhesion to a skin overlying the target. Adhesive means also are provided on both anterior and posterior borders of the base panel, which assists fastening of said base panel to the skin.

In one embodiment, the positioning guide assembly is configured to slidably and reversibly lock in a space provided in between of the outer shaft of the driven gear and the lock and release lever of the transducer housing enclosure. The horizontal slot of the rotation cylinder of the positioning guide assembly slides over the outer shaft of the driven gear and the lock and release lever couples with the horizontal slot of the rotation cylinder holder, which immobilizes the positioning guide assembly. In another embodiment, the positioning guide assembly is configured to be detachable from the positioning guide control assembly. Retracting the lock and release lever from the horizontal slot of the rotation cylinder holder allows said rotation cylinder holder to fasten the rotation cylinder and releases the positioning guide assembly from said positioning guide control assembly.

In one embodiment, a distance (a) from a proximal portion of the transducer to a center of a target is calculated by a substantially tangential placement of a center of the proximal portion of the transducer to a skin overlying the target. A horizontal distance from the center of the proximal portion of the transducer to a rotation center of the rotation cylinder of the positioning guide assembly is fixed as (b). Using a simple trigonometry, a distance (h) of a needle from the rotation center of the rotation cylinder to the center of the target equals a square root of $(a^2+b^2)$ and a sine of an angle ($\alpha$) of the rotation cylinder is calculated as a ratio of (a) to (h).

In one embodiment, the rotatable knob is configured to put numerical information of a measured distance (a) into the electronic control circuit, to rotate the rotation cylinder of the positioning guide assembly to a certain angle ($\alpha$) in relation to the horizontal axis of the proximal portion of the transducer head and to get locked in to prevent unintended rotation of said rotatable knob. The segment digital display shows at least two lines of numerical information, i.e., distance (a) and angle ($\alpha$). Input function of the rotatable knob is changeable by a plurality of pulled-out positions of the rotatable knob along the input shaft of the gearbox. The rotatable knob is pulled out to an outermost position along the input shaft to put in numerical information of a distance (a). The electronic control circuit automatically calculates an angle ($\alpha$) and displays numerical information of an angle ($\alpha$) in the segment digital display. A first inward position of the rotatable knob from the outermost position allows said rotatable knob to get engaged with the input shaft of the gearbox and to rotate the driving gear. In a manual model of the apparatus, rotation of the knob is measured by the angle dial displayed on the outer wall of the positioning guide controller assembly. In an electronic model of the apparatus, angle calculation is accomplished by the angle encoder axially connected to the rotatable knob via the input shaft. In one embodiment, the electronic control circuit is configured to display numerical data of an angle that decreases to zero upon rotation of the rotatable knob to come to an intended angle of the rotation cylinder for insertion of a needle through the tubular positioning guide into the target. A second inward position of the rotatable knob locks in said knob to avoid further rotation of said knob.

In one embodiment, the tubular positioning guide is provided in one or a plurality of configurations for a plurality of functions of said tubular positioning guide. For conventional needle biopsy procedures, the tubular positioning guide is provided with a range of fixed gauges of an inner tubular space to accommodate a range of sizes of needles. For inserting vascular devices and their accessories, the tubular positioning guide is provided as semicircular tubular, which is to allow open access and insertion of more than one device during one session of a procedure and unobstructed interchangeable removal of devices. For therapeutic procedures such as insertion of a probe for radiofrequency ablation of a lesion, for an example, the tubular positioning guide is provided with devices to fasten such probes at an angle for a duration of therapy.

BRIEF DESCRIPTION OF THE DRAWINGS

FIG. 1 shows a schematic example of the positioning guide assembly of the apparatus.

FIG. 2 shows a schematic example of individual parts of the positioning guide assembly: FIG. 2A represents a cross-sectional view of a rotation cylinder holder; FIG. 2B shows an exploded view with individual components except a tubular positioning guide; FIG. 2C shows the tubular positioning guide attached to a rotation cylinder and a stabilizer cylinder in a cross configuration; FIG. 2D shows an example of a semicircular tubular positioning guide.

FIG. 3 shows a schematic example of individual assemblies of the apparatus.

FIG. 4 shows a schematic example of the positioning guide control assembly.

FIG. 5 shows a schematic example of a three-quarter frontal view of the positioning guide control assembly; FIG. 5A shows an example of a layout of both the lock and release lever and output shaft of the gearbox; FIG. 5B shows an exploded view of both the lock and release lever and output shaft; FIG. 5C shows individual connecting components of the transducer housing enclosure and of a medial sidewall of the positioning guide controller assembly.

FIG. 6 shows a schematic example of the positioning guide controller assembly and of methods of using a rotatable knob.

FIG. 7A shows an exposed view of the bottom panel; FIG. 7B shows a solid gel panel that slides into an open space of the bottom panel; FIG. 7C shows a top-down view of the bottom panel.

FIG. 8 illustrates a schematic example of a mechanism of locking and unlocking of the positioning guide assembly.

FIG. 10 shows a schematic example of a sequence of using the apparatus of the present invention.

DETAILED DESCRIPTION OF THE DRAWINGS

As described below, the present invention provides a positioning guide apparatus and methods of use. It is to be understood that the descriptions are solely for the purposes of illustrating the present invention, and should not be understood in any way as restrictive or limited. Embodiments of the present invention are preferably depicted with reference to FIGS. 1 to 11, however, such reference is not intended to limit the present invention in any manner. The drawings do not represent actual dimension of devices, but illustrate the principles of the present invention.

Figure 1B:
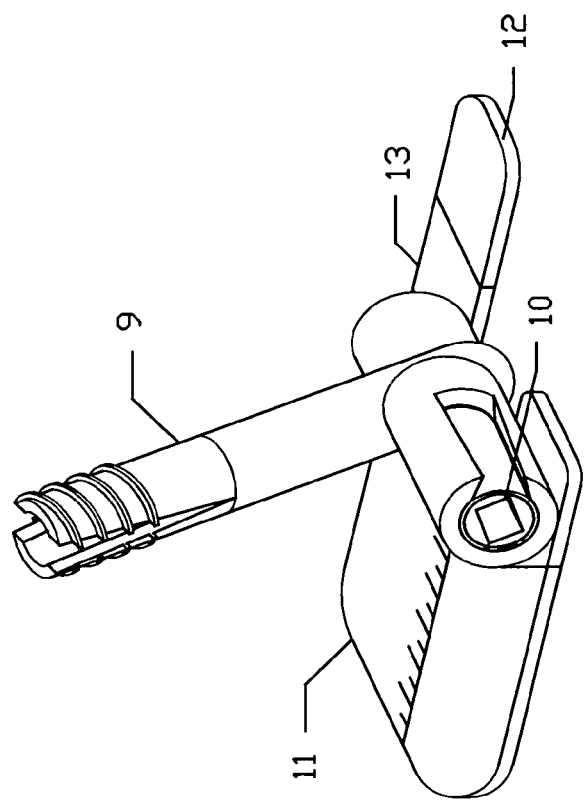
FIG. 1B represents an unfolded and angled positioning guide assembly detached from the transducer housing enclosure.
Figure 1A:
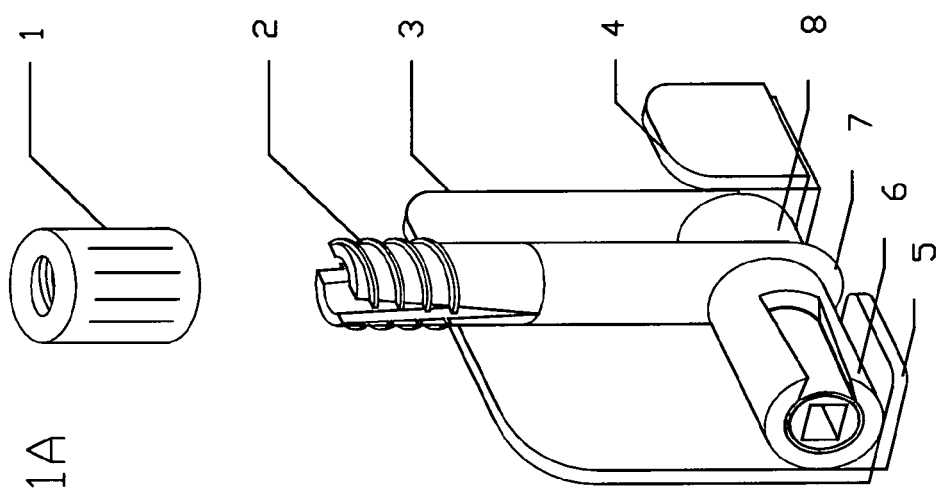
FIG. 1A represents a folded-up positioning guide assembly prior to attachment to a transducer housing enclosure of the apparatus.

FIG. 1 shows a schematic example of the positioning guide assembly of the apparatus. FIG. 1A represents a folded-up positioning guide assembly prior to attachment to a transducer housing enclosure of the apparatus. In this particular example, the positioning guide assembly comprises a threaded tubular guide 2 in an upright position with its tip 7 pointing down, an internally threaded cap 1 that rotatably fastens a threaded part of said tubular guide 2, a pair of folded-up attachment panels 3 and 4, one of a pair of bottom plates 5, a rotation cylinder holder 6 and a stabilizer cylinder holder 8. Both the rotation and stabilizer cylinder holders are not attached to the tubular body 9 but irreversibly attached to an upper surface of the bottom plates. FIG. 1B shows a fully deployed positioning guide assembly following detachment from the transducer housing enclosure. A tubular body 9 of the threaded tubular guide is rotated around a longitudinal axis of a rotation cylinder assembly 10 and fixed at an angle. The folded-up panels 3 and 4 are unfolded to become an anterior attachment panel 11 and a posterior attachment panel 12, respectively. The other bottom panel 13 is visible in this view. A lower surface of both the attachment panels and bottom plates has a means such as an adhesive to reversibly adhere to a skin.

FIG. 2 shows a schematic example of individual parts of the positioning guide assembly: FIG. 2A represents a cross-sectional view of the rotation cylinder holder 6. The rotation cylinder holder is provided in one or a plurality of tubular configurations having an outer wall 14, an inner wall 15 and a inner tubular space 21. The rotation cylinder holder has one part of a tubular wall cut out to form a horizontal slot bordered by a pair of horizontal edges 17 and 18. A plurality of horizontally linear threads 16, 19 and 20 are irreversibly attached to the inner wall, which is configured to provide firm grasp of a rotation cylinder. FIG. 2B shows an exploded view of individual components except the tubular positioning guide. The rotation cylinder holder 6 runs horizontally from a lateral end 22 that faces a vertical sidewall of the positioning guide controller assembly to a medial end 24 that faces the outer wall of the tubular positioning guide of the positioning guide assembly. On the outer wall of the rotation cylinder holder 6, a plurality of vertical pins 23 are provided to irreversibly get locked in a corresponding pin slot 29 of the bottom panel 5, which anchors the rotation cylinder holder irreversibly to the bottom panel. On the opposite side of the rotation cylinder holder, a stabilizer cylinder holder 8 runs horizontally from a medial end 26 that faces the outer wall of the tubular positioning guide to a lateral end 28. The stabilizer cylinder holder is provided in one or a plurality of tubular configurations having an inner tubular space 25 and a plurality of vertical pins 27 that get irreversibly locked in a corresponding pin slot 30 of the bottom panel 13. In between of both the bottom plates 5 and 13, an open space is provided to accommodate the tip of the tubular positioning guide. The open space is bordered anteriorly by a recess 31 of the anterior attachment panel 11. FIG. 2C shows the tubular positioning guide 9 irreversibly attached to a rotation cylinder 34 and a stabilizer cylinder 35 in a cross configuration. Inside the rotation cylinder 34, a longitudinal slot 33 is provided to reversibly accommodate a rotatable shaft. The rotation cylinder is encased by a thin nonslip tubular elastomer 32 which is located in between of an outer wall of the rotation cylinder and the inner wall of the rotation cylinder holder and which provides friction on both the walls. FIG. 2D shows an example of a semicircular tubular positioning guide which has a body portion 37 having a configuration of an open semicircular tubular conduit 38 bordered by a proximal tip 39 and a distal end 36.

Figure 3B:
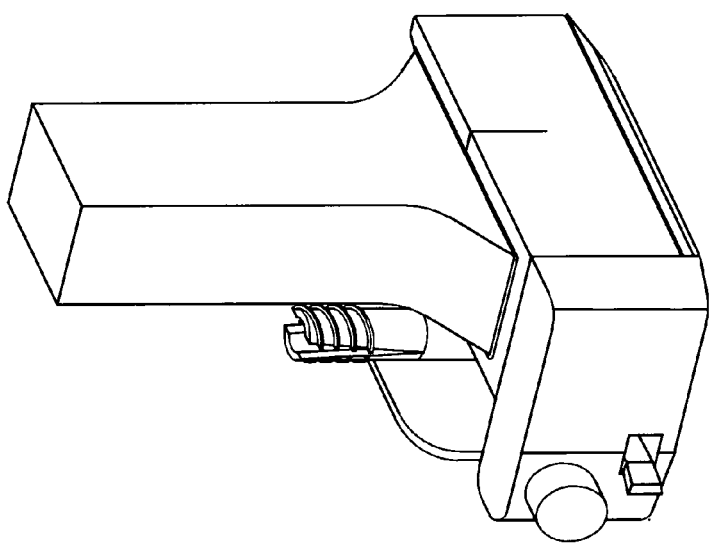
FIG. 3B shows a fully assembled view of the apparatus with the transducer head in place.
Figure 3A:
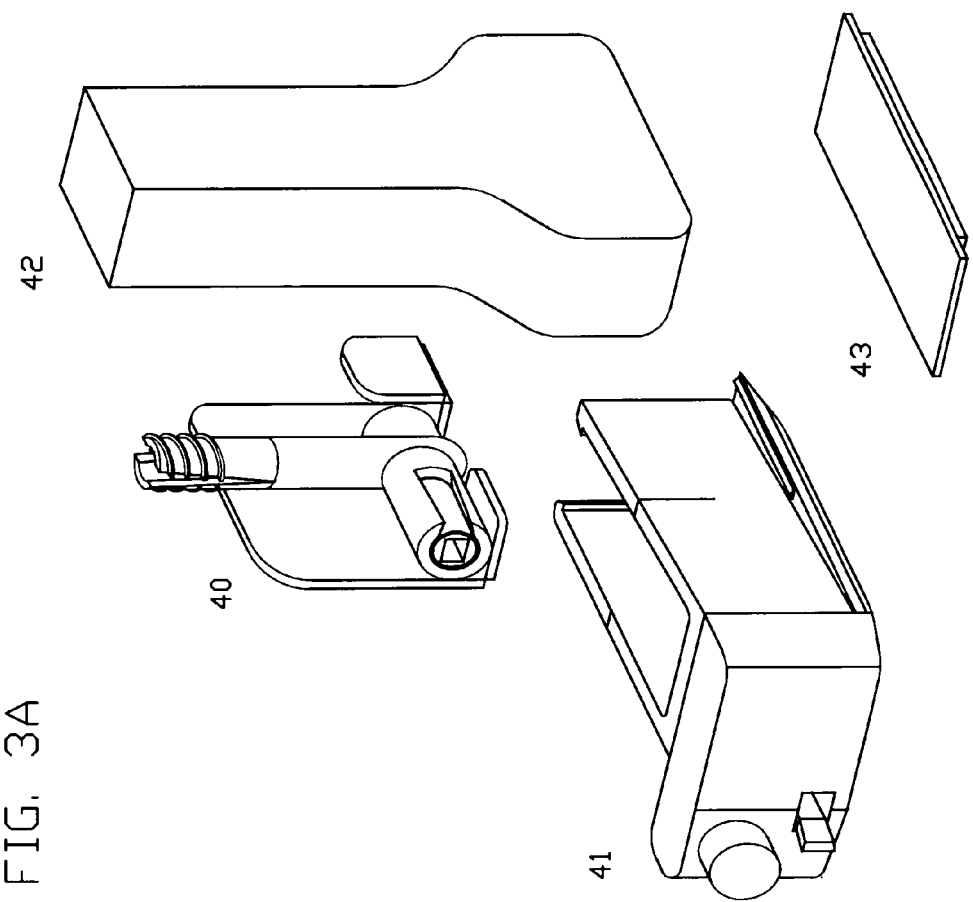
FIG. 3A shows a positioning guide assembly, a positioning guide control assembly, an ultrasound transducer head and a solid gel panel.

FIG. 3 shows a schematic example of individual assemblies of the apparatus. FIG. 3A shows a positioning guide assembly 40, a positioning guide control assembly 41, an ultrasound transducer head 42 and a solid gel panel 43. FIG. 3B shows a fully assembled view of the apparatus with the transducer head 42 in place. The positioning guide assembly 41 is reversibly attachable to a proximal portion of a medial sidewall of the positioning guide control assembly 41 and the solid gel panel 43 is placed below a face of the transducer head 42 inside an open space provided in the positioning guide control assembly 41. The transducer head 42 slides in and gets reversibly fastened to the positioning guide control assembly 41. Both the positioning guide assembly 40 and solid gel panel 43 are non-reusable.

FIG. 4 shows a schematic example of the positioning guide control assembly. FIG. 4A shows a three-quarter view of the positioning guide control assembly, which comprises a positioning guide controller assembly 44 having a proximal end 45 and a distal end 46, and a transducer housing enclosure 50 having an anterior sidewall 49, a posterior sidewall 51, a pair of vertical lateral edges 52 and 53 and a bottom panel 55. On a lateral sidewall of the proximal portion of the positioning guide controller assembly 44, a rotatable knob 47 and a retractable knob 48 are located. The rotatable knob 47 is connected through the lateral sidewall to a gearbox via an input shaft. The retractable knob 48 is connected to a lock and release lever that runs through a horizontal conduit inside the positioning guide controller assembly. The anterior sidewall 49 of the transducer housing enclosure adjoins a medial sidewall of said housing enclosure at a right angle whereas the posterior sidewall 51 adjoins said medial sidewall at an oblique angle. The posterior sidewall 51 is bendable at a joint with the medial sidewall in a manner that a transducer head is held fast inside the transducer housing enclosure 50. Once the transducer head slidably is placed in the transducer housing enclosure, the posterior sidewall 51 reversibly is secured by a longitudinal securing ridge 54 that protrudes from the bottom panel 55.

Figure 4A:
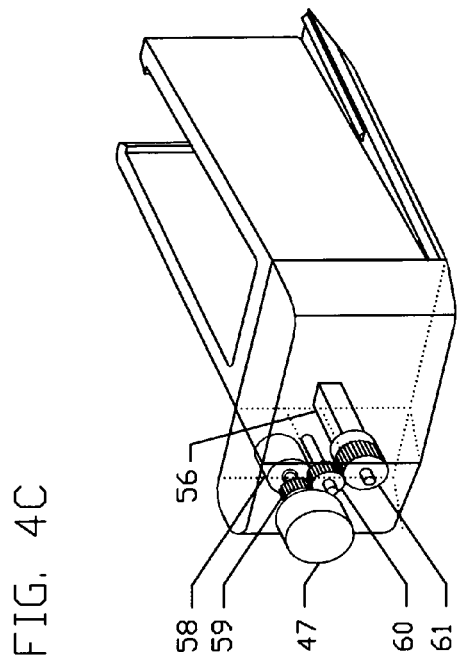
FIG. 4A shows individual compartments and parts of the positioning guide control assembly.
Figure 4D:
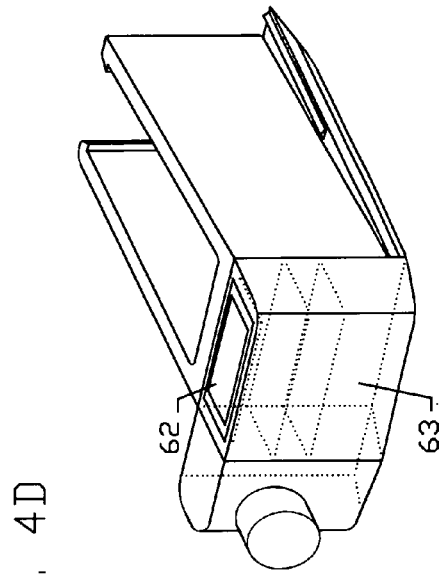
FIG. 4D shows a segment digital display and compartments of a power and electronic control assembly.
Figure 4B:
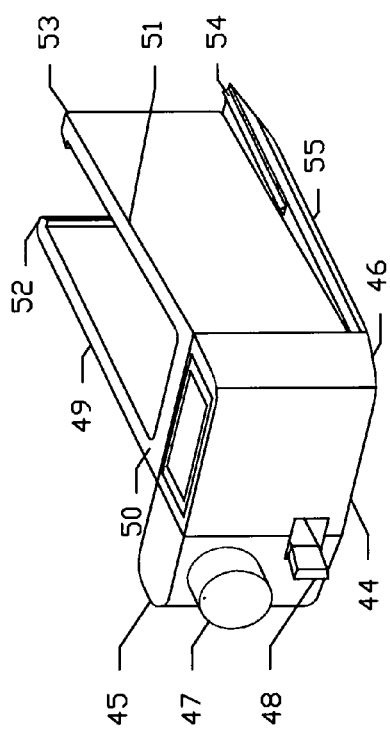
FIG. 4B shows an output shaft and a lock and release lever.
Figure 4C:
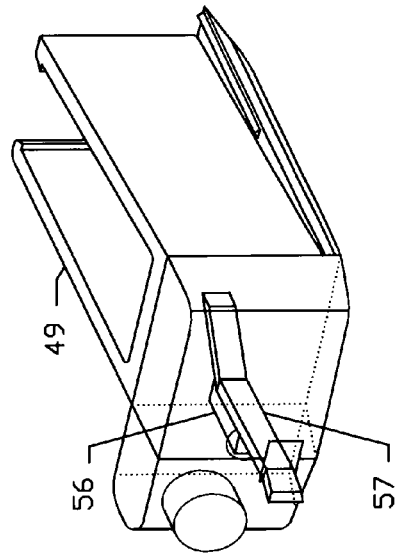
FIG. 4C shows a gearbox of a positioning guide controller assembly.

FIG. 4B shows a layout of an output shaft 56 and a lock and release lever 57. The output shaft 56 is provided as one or a plurality of configurations having more than two internal angles on a circumferential cross-section, which horizontally protrudes from the medial sidewall of the positioning guide controller assembly to a space in front of the anterior sidewall 49. The lock and release lever 57 is irreversibly attached to a lower portion of an outer surface of the anterior wall 49. FIG. 4C shows a gearbox of the positioning guide controller, which is provided in one or a plurality of configurations having a main driving gear 59 connected through an input shaft to a rotatable knob 47, a parallel driven gear 61 with its output shaft 56 and a pinion 60 located in between of the driving and driven gears. An angle encoder 58 axially is connected through the input shaft to the rotatable knob 47. FIG. 4D shows a segment digital display 62 and compartments of a power and electronic control assembly 63. An upper compartment houses an electronic circuit board and a lower compartment houses batteries. The segment digital display 62 is provided with a plurality of display lines for numerical data. The angle encoder 58, the segment digital display 62 and the power and electronic control assembly 63 are electrically connected.

FIG. 5 shows a schematic example of a three-quarter frontal view of the positioning guide control assembly. FIG. 5A shows both the lock and release lever 57 and output shaft 56 of the gearbox protruding from the medial sidewall of the positioning guide controller assembly. On the central portion of a lower border of the outer surface of the anterior sidewall 49, a vertical groove 65 is provided to allow unhindered passage of a needle in a tubular positioning guide guide at an angle to a target. The bottom panel of the transducer housing enclosure is bordered laterally by a lateral edge 64. FIG. 5B shows an exploded view of both the lock and release lever and output shaft. The lock and release lever 57 is provided in one or a plurality of materials and of configurations, which comprises a lever attachment portion 66, an angled portion 67, a straight portion 68 and a retractable knob 48. One of the materials for the lever 57 is metallic, having an elastic bending quality. The output shaft 56 comprises a proximal portion 69, a cylindrical portion 70 and the driven gear 61 along a longitudinal axis. Depicted in FIG. 5C1, the attachment portion 66 of the lever 57 of FIG. 5B2 is irreversibly fastened to an attachment recess 71 of an open slot 73 carved in the outer surface of the anterior sidewall 49. Both the angled and straight portions 67 and 68 of the lever 57 are located in front of the slot 73 and can be retracted posteriorly toward an inner wall 72 of the anterior sidewall 49 by horizontally pulling the retractable knob 48. Shown in FIG. 5C, an outer surface 75 of the medial sidewall of the transducer housing enclosure gets irreversibly connected to an outer surface 78 of a medial sidewall of the positioning guide controller assembly by a plurality of pin 76-slot 77 combinations. The slot 73 for the lever 57 merges with an aperture 79 of a lever conduit through which the straight portion 68 and the retractable knob 48 of the lever 57 pass. The knob 48 exits to the outer surface of the lateral sidewall of the positioning guide controller. Horizontally in front of the aperture 79, a round aperture 80 is provided in the medial sidewall of the controller assembly to accommodate the cylindrical portion 70 of the output shaft 56. On an inner surface of the medial sidewall of the transducer housing enclosure, an electric switch 74 is provided, which is reversibly pushable by an incoming transducer head to the enclosure and which electrically activates the apparatus.

Figure 6A:
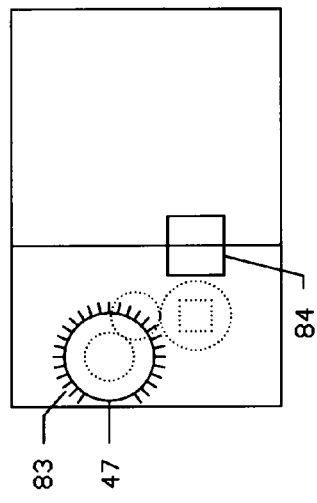
FIG. 6A illustrates a see-through view of the gearbox and the segment digital display.
Figure 6C:
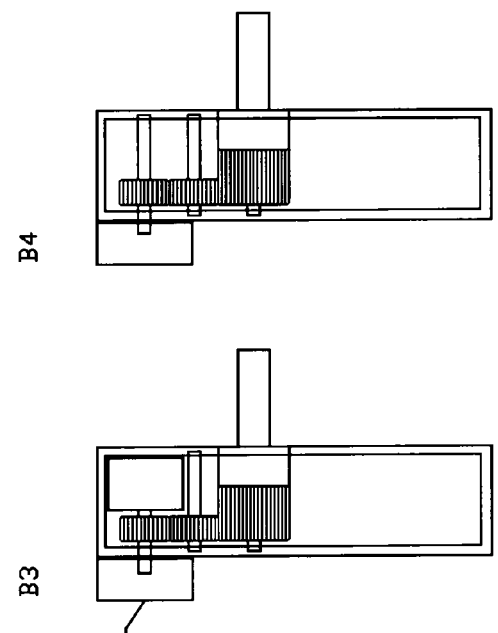
FIG. 6C shows a schematic presentation of a dial marked around the rotatable knob.
Figure 6B:
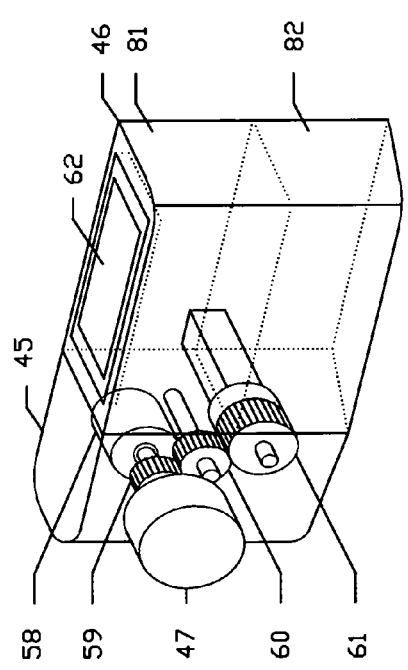
FIG. 6B shows an electronic configuration and a manual configuration of the positioning guide controller, and a sequence of positioning of the rotatable knob in an electronic configuration.
Figure 7B:
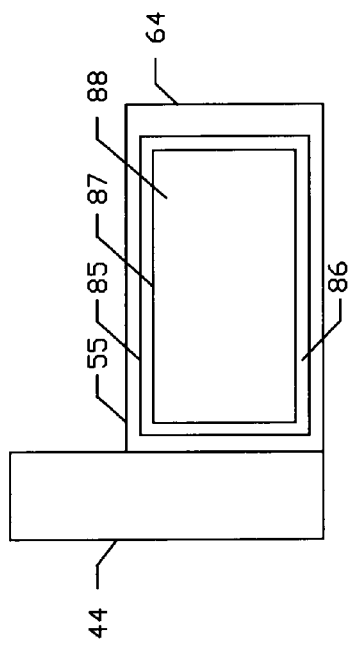
FIGS. 7A-7C show a schematic example of a configuration of a bottom panel of the transducer housing enclosure.
Figure 7D:
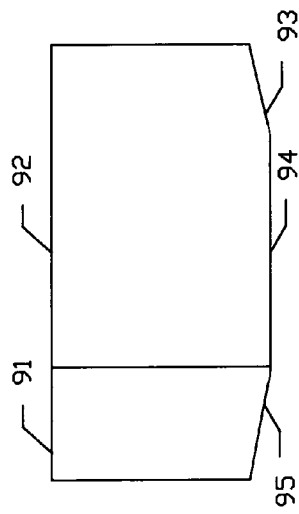
FIG. 7D shows a profile view of the positioning guide controller assembly.
Figure 7A:
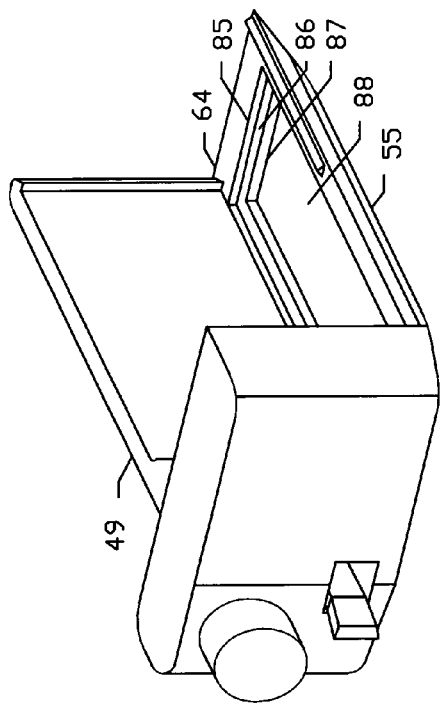
Figure 7C:
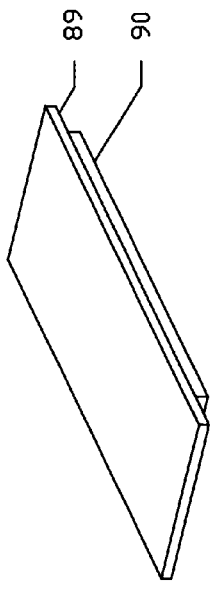
Figure 8A:
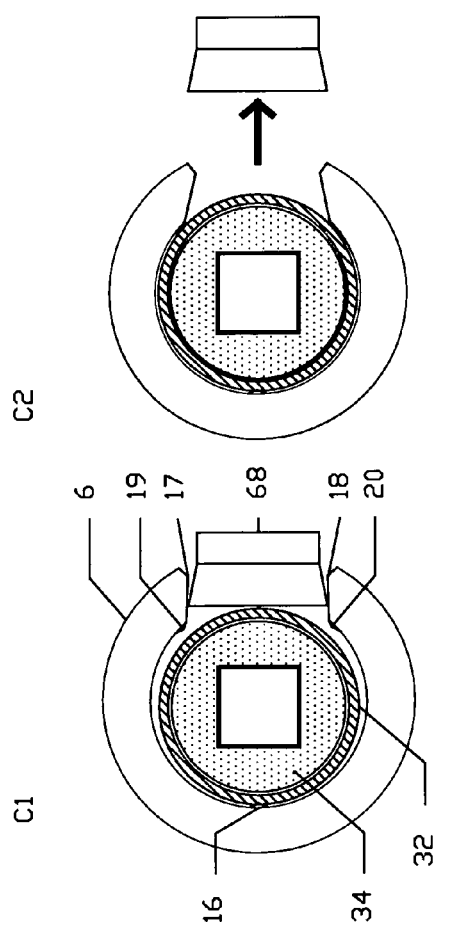
FIG. 8A shows individual components for the locking and unlocking mechanism.
Figure 8C:
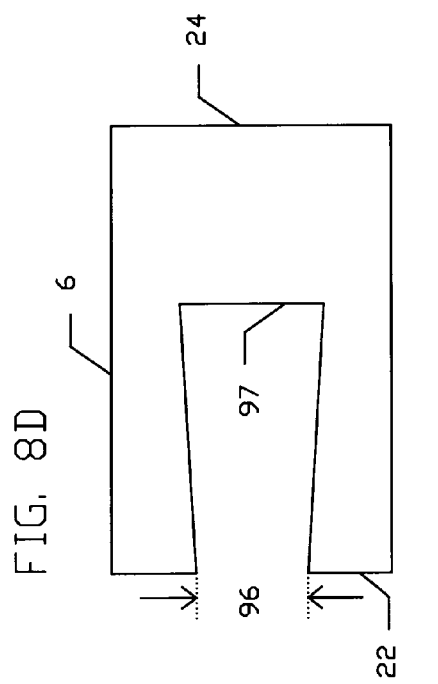
FIG. 8C depicts an example of the locking and unlocking mechanism.
Figure 8D:
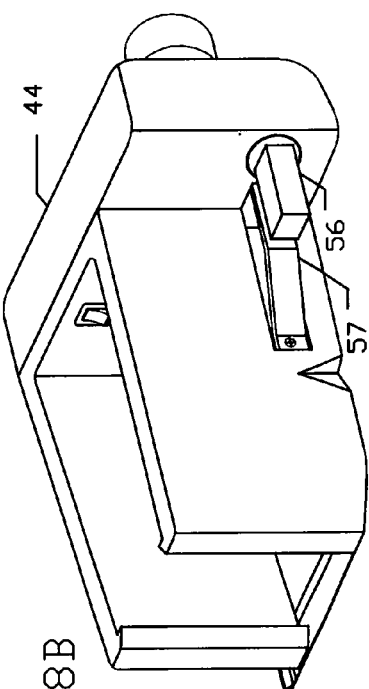
FIG. 8D shows a profile view of a horizontal slot of the rotation cylinder holder.
Figure 8B:
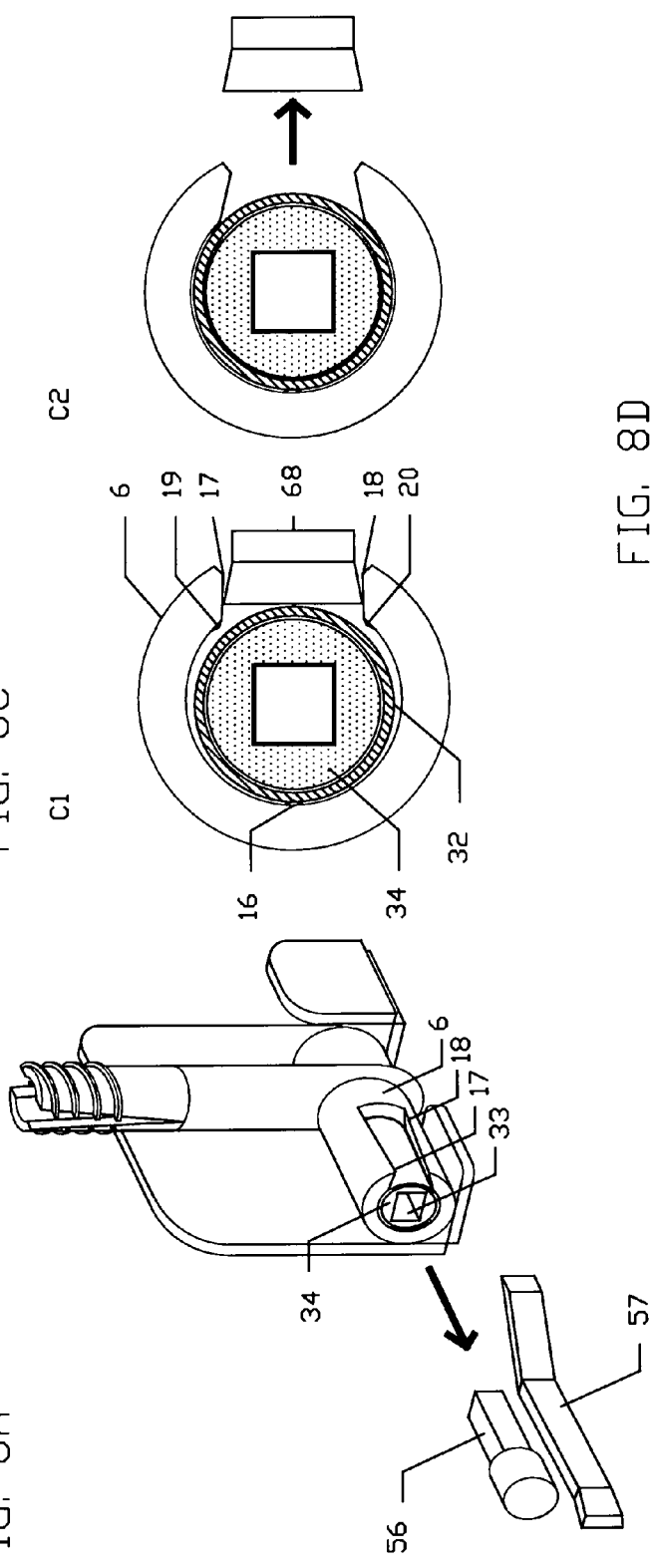
FIG. 8B shows a spatial arrangement of the components of the positioning guide control assembly.

FIG. 6 shows a schematic example of the positioning guide controller assembly and of methods of using the rotatable knob. FIG. 6A illustrates a see-through view of the gearbox, the segment digital display and the upper 81 and lower compartments 82 of the power and electronic control assembly. FIGS. 6B1 through B3 show an electronic configuration of the guide controller with the angle encoder 58 axially connected to the rotatable knob 47 and FIG. 6B4 shows a manual configuration of the guide controller without an angle encoder. In FIG. 6B1, the rotatable knob 47 is pulled out to an outermost position along the input shaft, which makes said rotatable knob disengaged from the input shaft of the gearbox and which allows rotation of the rotatable knob 47 to display numerical data of a distance from a proximal portion of a transducer to a target on the segment digital display 62. Once the numerical data of the distance is put in the electronic circuit board, the electronic circuit board calculates an acute angle between a horizontal axis of the transducer head and a longitudinal axis of the tubular positioning guide and displays the numerical information of the acute angle in the segment digital display. FIG. 6B2 illustrates first inward positioning of the rotatable knob from the outermost position, which allows said rotatable knob to get engaged with the input shaft and to rotate the driving gear 59 and a rotating axis of the angle encoder 58 simultaneously. Rotation of the rotatable knob 47 in the first inward position rotates the driven gear 61 and is configured to decrease the displayed angle in the segment digital display to zero when the output shaft 56 comes to an intended angle for the rotation cylinder 34 of FIG. 2. FIG. 6B3 schematically shows a locked rotatable knob in a second inward position of said rotatable knob to avoid further rotation of said knob. An angle dial 83 in FIG. 6C is marked on the lateral sidewall of the positioning guide controller for a manual model, which illustratively measures rotation of the knob 47. FIG. 6C also shows a schematic view of an outer aperture 84 for the lock and release lever 57 of FIG. 5.

FIG. 7 shows a schematic example of a configuration of a bottom panel of the transducer housing enclosure and a profile view of the positioning guide controller assembly. FIG. 7A shows an exposed view of the bottom panel 55, with both the posterior sidewall and medial sidewall of the transducer housing enclosure removed for illustration. FIGS. 7A and 7B show a rectangularly open central space 88 that is surrounded by an inner edge 87. The inner edge 87 is outwardly bordered by a solid gel panel holding frame 86. The holding frame 86 is a flat depression surrounded by an outer edge 85 of the bottom panel, which is configured to hold the solid gel panel. The bottom panel 55 is laterally bordered by the lateral edge 64 and medially by a medial sidewall of the positioning guide controller 44. FIG. 7C shows a schematic example of the solid gel panel having a larger upper portion 89 and a lower portion 90. The upper portion 89 contacts the transducer face and sits on the holding frame 86 and the lower portion 90 is inserted in the open central space 88 and contacts a skin of a patient. FIG. 7D illustrates an example of a profile view having an upper border 91 and a lower border 95 of the positioning guide controller assembly, and an upper border 92 and lower borders 94 and 93 of the power and electronic control assembly. Both the lower borders 95 and 93 are obtusely angled to the straight lower border 94, which is configured to allow the positioning guide control assembly to roll back and forth on a skin in anterior-to-posterior direction.

FIG. 8 illustrates a schematic example of a mechanism of locking and unlocking of the positioning guide assembly. In FIGS. 8A and 8B, the longitudinal slot 33 of the rotation cylinder 34 reversibly slides over the output shaft 56 of the positioning guide controller 44. The lock and release lever 57 slides in the horizontal slot of the rotation cylinder holder 6 bordered by both the horizontal edges 17 and 18 and provides the positioning guide assembly with an attachment to the positioning guide control assembly. FIG. 8C1 illustrates an example of a mechanism of unlocking of the rotation cylinder 34 by inserting the straight portion 68 of the lock and release lever 57 to the horizontal space between the edges 17 and 18. The horizontal slot is reversibly and circumferentially expandable to a degree upon engagement with the straight portion 68, which widens the inner tubular space of said rotation cylinder holder 6. Widening of the inner tubular space allows friction-less rotation of both the elastomer 32 and rotation cylinder 34 inside said rotation cylinder holder 6. FIG. 8C2 shows a mechanism of locking of the rotation cylinder 34 by disengagement of the straight portion 68 of the lock and release lever from the horizontal slot, which shrinks the widened circumference of said tubular space. The shrunk rotation cylinder holder 6 then holds fast both the tubular elastomer 32 and rotation cylinder 34 together. The rotation cylinder 34 is fastened by friction generated by the circumferentially squeezed tubular elastomer 32 encasing said rotation cylinder. The linear threads 16, 19 and 20 located on the inner wall of the rotation cylinder holder 6 assist fastening of the elastomer 32 by said rotation cylinder holder 6. FIG. 8D shows a profile view of a trapezoidal configuration of the horizontal slot of the rotation cylinder holder 6. A medial side 96 located on the border 22 of the rotation cylinder holder 6 is shorter than a lateral side 97 on the border 24 of said holder 6, which is configured to tighten coupling of the rotation cylinder holder 6 with the lock and release lever 57.

Figure 9A:
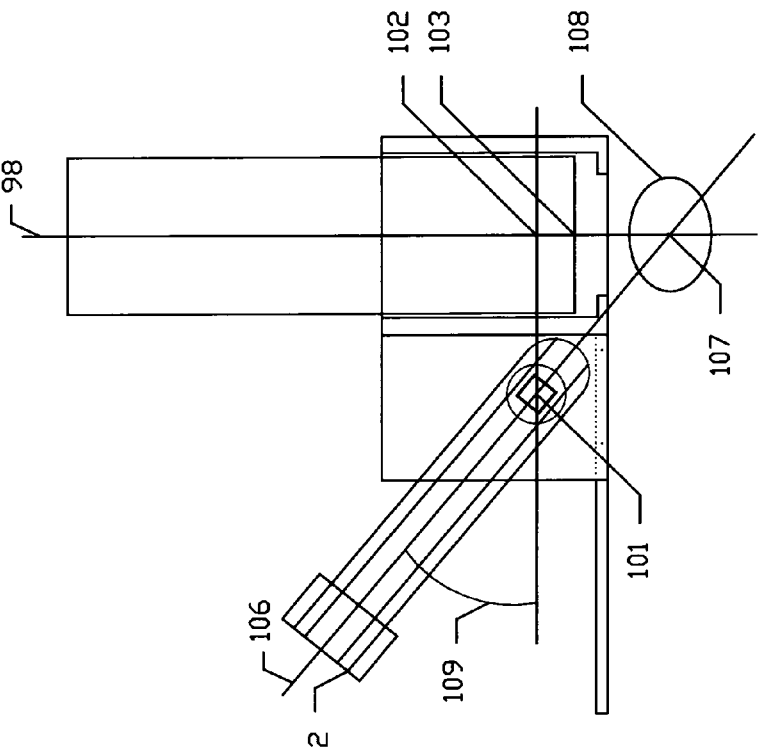
FIGS. 9A & 9B depict schematic examples of variable trigonometric angulation of the tubular positioning guide and variable distance from a rotation center of the rotation cylinder to a center of the target.
Figure 9B:
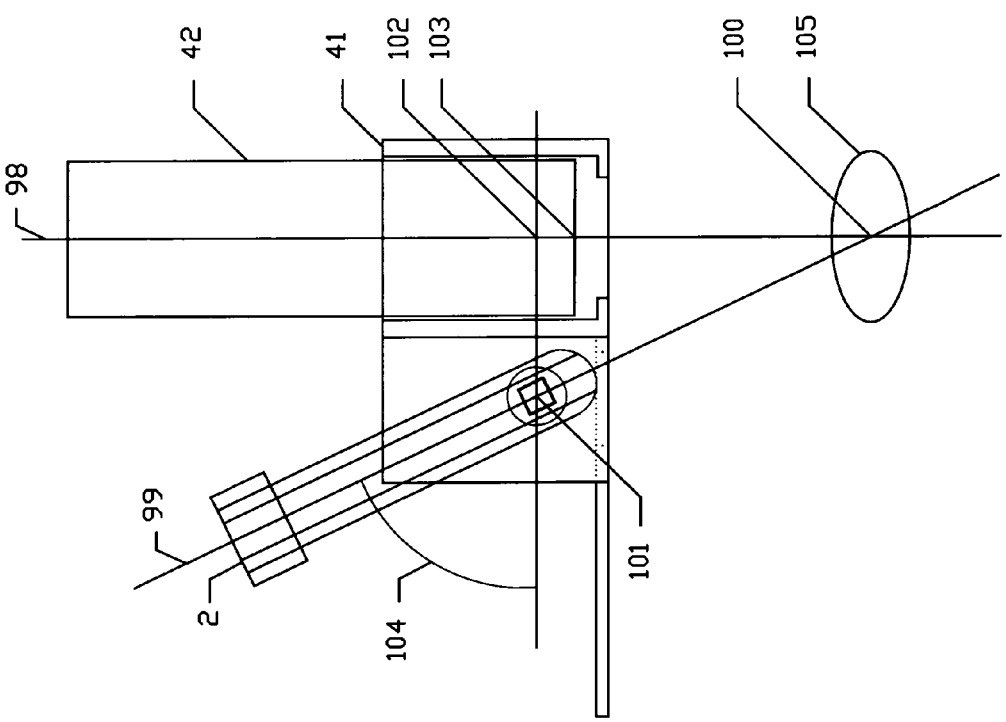
Figure 10A:
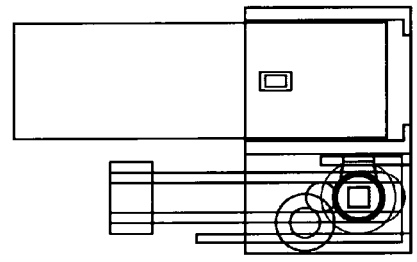
FIG. 10A shows components of individual components of the apparatus and a transducer head.
Figure 10B:
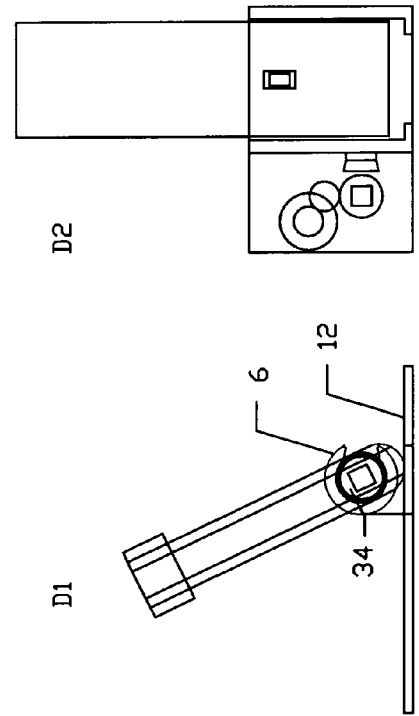
FIG. 10B shows a fully assembled apparatus with the transducer head.
Figure 10C:
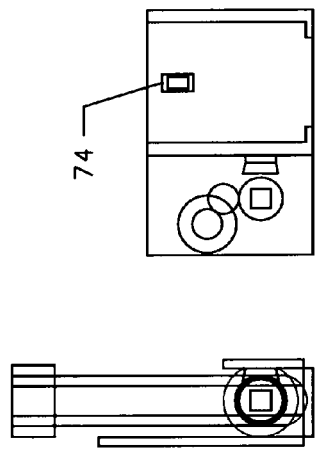
FIG. 10C shows a unfolded and rotated positioning guide assembly.
Figure 10D:
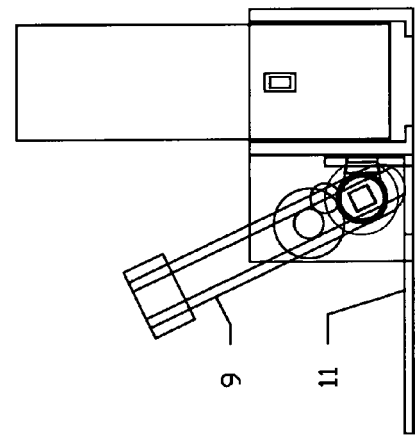
FIG. 10D shows a detached and fully deployed positioning guide assembly.
Figure 11D:
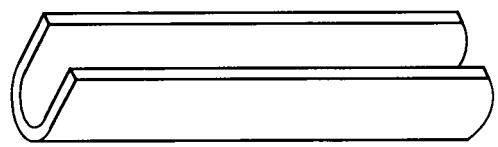
FIG. 11 illustrates schematic examples of various configurations of the tubular positioning guide.
Figure 11C:
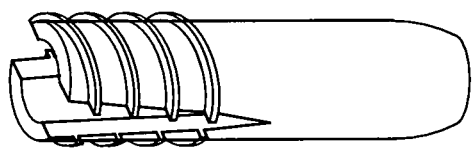
Figure 11B:
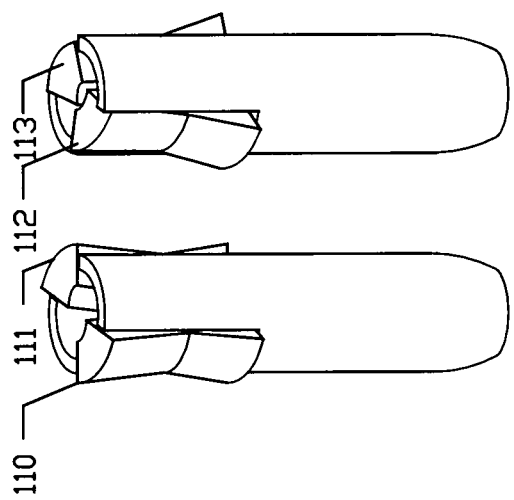
Figure 11A:
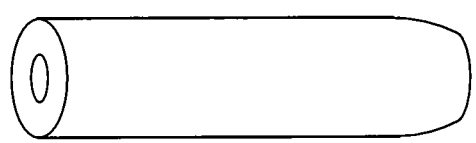

FIGS. 9A & 9B depict schematic examples of variable trigonometric angulation of the tubular positioning guide and variable distance from a rotation center of the rotation cylinder to a center of a target. In FIG. 9A, a substantially vertical distance (a) is calculated as a sum of a distance from a center 103 of the face of the transducer 42 to a center 100 of a target 105 along a longitudinal axis 98 measured by ultrasonogram and a fixed value of a vertical distance from a point 102 on the longitudinal axis 98 crossing a horizontal line connecting a rotation center 101 of the rotation cylinder with the transducer head to the point 103. A horizontal distance between the rotation center 101 and the point 102 is calculated as (b), which is a fixed value. A distance (h) of a needle from the rotation center 101 to the center 100 of the target 105 is calculated as a square root of $(a^2+b^2)$ and a sine of an angle ($\alpha$) 104 between a longitudinal axis 99 of the tubular guide 2 and the horizontal line of the rotation cylinder is calculated as a ratio of (a) to (h). FIG. 9B shows a target 108 located closer to the transducer face, compared to the example in FIG. 9A. Accordingly the distance from the point 102 to a center 107 of a target 108 is shorted than that in FIG. 9A and an angle 109 between a longitudinal axis 106 of the tubular guide and the horizontal line crossing the rotation center 101 is more acute that that in FIG. 9A.

FIG. 10 shows a schematic example of a sequence of methods using the apparatus of the present invention. In FIG. 10A, FIG. A1, FIG. A2 and FIG. A3 represent a positioning guide assembly, a positioning guide control assembly and a transducer head, respectively. Once fully assembled with the transducer head inside the positioning guide control assembly and placed on a skin overlying a target shown in FIG. 10B, the apparatus rotates a tubular guide 9 toward the target based on a set of numerical data of a length and an angle of a needle to reach the target. After locking of the rotation of the tubular guide 9, an anterior attachment panel 11 is unfolded and attached to the skin overlying the target, as shown in FIG. 10C. Following the attachment of the positioning guide assembly to the skin, the positioning guide assembly is detached from the positioning guide assembly, as shown in FIG. 10D. A rotation cylinder 34 of the rotated tubular guide is fastened by a rotation cylinder holder 6, which prevents unintended rotations. Finally a posterior attachment panel 12 is unfolded and attached to the skin, thereby stabilizing the positioning guide assembly.

FIG. 11 illustrates schematic examples of various configurations of the tubular positioning guide of the apparatus of the present invention. For conventional needle biopsy procedures, FIG. 11A shows a configuration for a range of fixed gauges of an inner tubular space to accommodate a range of sizes of needles. FIGS. 11B and 11C show configurations of a tubular body to fasten needles and probes for diagnostic and therapeutic purpose which requires a steady maintenance of a position of a needle or a probe for a duration of the procedure. One example uses a pair of depressible knobs 110 and 111 located longitudinally in a tubular wall, as shown in FIG. 11B1. An internal lumen of the tubular guide is narrowed by pushing the pair of the depressible knobs 112 and 113, which holds fast a needle inside the internal lumen. Another example uses a cap with internal threads which rotatably narrow an internal lumen of a threaded tubular guide and fasten a needle inside said tubular guide. FIG. 11D shows a configuration of a semi-circular tube which allows an open access to said tubular guide and insertion of more than one device during one session of a procedure and unobstructed interchangeable removal of devices.

It is to be understood that the aforementioned description of the apparatus and methods is simple illustrative embodiments of the principles of the present invention. Various modifications and variations of the description of the present invention are expected to occur to those skilled in the art without departing from the spirit and scope of the present invention. Therefore the present invention is to be defined not by the aforementioned description but instead by the spirit and scope of the following claims.

What is claimed is:

1. A positioning guide apparatus, comprising:
a positioning guide assembly, and a positioning guide control assembly;
the positioning guide assembly, wherein the positioning guide assembly comprises a tubular positioning guide, a rotation cylinder assembly and a securing base, wherein the rotation cylinder assembly comprises a rotation cylinder and a rotation cylinder holder, wherein the rotation cylinder holder comprises an open slot disposed thereof on a cylindrical overtube of the rotation cylinder holder, wherein the positioning guide assembly is configured to let the rotation cylinder be rotatable by coupling the positioning guide assembly with the positioning guide control assembly for operational control of the positioning guide assembly by the positioning guide control assembly, wherein the positioning guide assembly is configured to lock the rotation cylinder by uncoupling the positioning guide assembly from the positioning guide control assembly so as to guide an invasive tubular device inside the positioning guide assembly slidably passing therethrough in a range of insertion angle to a tissue target; and
the positioning guide control assembly, wherein the positioning guide control assembly comprises a positioning controller assembly, a power and electronic control assembly and an ultrasound transducer enclosure, wherein the positioning controller assembly comprises a lock and release lever and a gearbox arrangement connected to an output shaft and a rotatable knob, wherein the lock and release lever is configured to reversibly couple with the open slot of the rotation cylinder holder, wherein the output shaft of the gearbox arrangement is configured to reversibly and coaxially couple with the rotation cylinder of the positioning guide assembly, wherein the power and electronic control assembly is configured to display numerical information about angular displacement of the rotation cylinder and distance from a rotation center of the rotation cylinder to the tissue target, and wherein the power and electronic control assembly is configured to display numerical data of an angle that decreases to zero upon rotation of the rotatable knob to come to an intended angle of the rotation cylinder for insertion of a needle through the tubular positioning guide into the tissue target and wherein the positioning guide assembly further comprises:

a tubular positioning guide, wherein the tubular positioning guide comprises a tubular conduit configured to fixedly join the rotation cylinder of the rotation cylinder assembly at a right angle, wherein the tubular conduit is configured to slidably pass the invasive tubular device therethrough to reach the tissue target, and wherein the tubular positioning guide is configured to rotate about a joint with the rotation cylinder manually driven by the gearbox arrangement of the positioning guide control assembly; and the rotation cylinder assembly, wherein the rotation cylinder assembly comprises the rotation cylinder, the rotation cylinder holder and a nonslip tubular elastomer, wherein the rotation cylinder is configured to be tightly encircled by the nonslip tubular elastomer, wherein the rotation cylinder is configured to coaxially mate with an output shaft of the gearbox arrangement and to be coaxially rotatable by the output shaft of the gearbox arrangement, wherein the rotation cylinder encircled by the nonslip tubular elastomer is rotatably housed in the rotation cylinder holder, wherein the open slot of the cylinder overtube of the rotation cylinder holder is configured to reversibly couple with and uncouple from the lock and release lever of the positioning guide control assembly, wherein the coupling of the open slot of the cylinder overtube with the lock and release lever is configured to let the rotation cylinder be rotatable so as to rotationally adjust the tubular positioning guide for the insertion angle of the invasive tubular device, wherein the uncoupling of the open slot of the cylinder overtube from the lock and release lever is configured to lock the rotation cylinder by the cylinder overtube so as to lock the tubular positioning guide for the insertion angle of the invasive tubular device, and wherein the nonslip tubular elastomer is configured to provide the rotation cylinder and the rotation cylinder holder with circumferential friction so as to concentrically fasten the rotation cylinder by the rotation cylinder holder.

2. The positioning guide apparatus according to claim 1, wherein the positioning guide control assembly further comprises:

the lock and release lever, wherein the lock and release lever comprises a proximal knob and an coupling portion connected to the proximal knob, wherein the coupling portion is configured to be inserted in the open slot of the cylindrical overtube of the rotation cylinder holder of the rotation cylinder assembly and to release the rotation cylinder of the rotation cylinder assembly from the cylindrical overtube so as to let the rotation cylinder be rotatable, wherein the coupling portion is configured to be released from the open slot of the cylindrical overtube so as to let the cylindrical overtube concentrically lock the rotation cylinder of the rotation cylinder assembly, and wherein the concentric locking of the rotation cylinder by the cylindrical overtube by the release of the coupling portion of the lock and release lever from the open slot of the cylindrical overtube is configured to release the positioning guide assembly from the positioning guide control assembly; and the ultrasound transducer enclosure, wherein the ultrasound transducer enclosure comprises a rocker-type electric switch disposed on an inner wall of the ultrasound transducer enclosure, and wherein the rocker-type electric switch is configured to be reversibly pushed in by an ultrasound transducer housed in the ultrasound transducer enclosure so as to turn on the positioning guide control assembly.

3. The positioning guide control assembly according to claim 1, wherein the positioning guide control assembly is configured to measure the trigonometric angle between the horizontal axis of the ultrasound transducer housed in the ultrasound transducer enclosure and the longitudinal axis of the tubular positioning guide of the positioning guide assembly by using the horizontal axis of the ultrasound transducer as a stationary reference;

wherein the manual rotation of the gearbox arrangement of the positioning guide control assembly is configured to pivot the longitudinal axis of the tubular positioning guide of the positioning guide assembly about the rotation cylinder of the positioning guide assembly; and wherein the positioning guide control assembly is configured to calculate the trigonometric angle by measuring a circular pivoted distance of the rotation cylinder of the positioning guide assembly.

4. A method of guiding an invasive tubular device to reach a tissue target, comprising:

providing a positioning guide apparatus comprising a positioning guide assembly and a positioning guide control assembly;

inserting a coupling portion of a lock and release lever of the positioning guide control assembly into an open slot of a rotation cylinder holder of the positioning guide assembly so as to couple the positioning guide assembly with the positioning guide control assembly, and simultaneously inserting an output shaft of a gearbox arrangement of the positioning guide control assembly into a slot of a rotation cylinder of a tubular positioning guide of the positioning guide assembly, wherein insertion of the lock and release lever of the positioning guide control assembly into the open slot of the rotation cylinder holder of the positioning guide assembly is configured to release the rotation cylinder of the tubular positioning guide from the rotation cylinder holder of the positioning guide assembly so as to let the tubular positioning guide be rotatable inside the rotation cylinder holder of the positioning guide assembly;

inserting an ultrasound transducer in an ultrasound transducer enclosure, wherein the insertion of the ultrasound transducer in the ultrasound transducer enclosure is configured to power up the positioning guide control assembly;

placing a proximal end of the positioning guide apparatus on a skin overlying a tissue target, wherein a flat wall of a securing base of the positioning guide assembly contacts the skin;

visualizing an area of the tissue target and the tissue target in a visualized ultrasonographic field of a main ultrasonographic machine;

measuring a distance from a point of the ultrasound transducer to a center of the tissue target and manually putting a numerical information of the distance in a power and electronic control assembly by rotating a rotatable knob of a positioning controller assembly of the positioning guide control assembly, wherein the rotatable knob is configured to be in a first position for putting in the numerical information, wherein the power and electronic control assembly is configured to display on the positioning guide control assembly a trigonometric angle between a horizontal axis of the ultrasound transducer housed in the ultrasound transducer enclosure and a longitudinal axis of the tubular positioning guide of the positioning guide assembly by using the measured numerical information of the distance;

rotating the rotatable knob of the positioning guide control assembly to rotatably pivot the rotation cylinder of the tubular positioning guide of the positioning guide assembly so as to align the longitudinal axis of the tubular positioning guide with the tissue target;

uncoupling the lock and release lever of the positioning guide control assembly from the open slot of the rotation cylinder holder so as to let the rotation cylinder of the tubular positioning guide be locked by the rotation cylinder holder, wherein the uncoupling of the lock and release lever from the open slot of the rotation cylinder holder is configured to uncouple the positioning guide assembly from the position guide control assembly, and wherein the uncoupling of the open slot of the rotation cylinder holder from the lock and release lever is configured to lock the rotation cylinder by the rotation cylinder holder so as to lock the tubular positioning guide at an angle, and wherein a nonslip tubular elastomer is configured to provide the rotation cylinder and the rotation cylinder holder with circumferential friction so as to concentrically fasten the rotation cylinder by the rotation cylinder holder; and detaching the positioning guide control assembly from the positioning guide assembly, wherein the flat wall of the securing base of the positioning guide assembly is securely adhered to the skin overlying the tissue target, wherein the tubular positioning guide of the positioning guide assembly is immovably aligned with the tissue target in a way the longitudinal axis of the tubular positioning guide intersects the tissue target at the trigonometric angle so as to direct the invasive tubular device to the tissue object through the tubular positioning guide.

* * * * *